United States Patent [19]
Stowers

[11] Patent Number: 6,065,563
[45] Date of Patent: May 23, 2000

[54] BELT-MOUNTED STETHOSCOPE SUPPORTING DEVICE

[76] Inventor: Karen S. Stowers, Rte. 1 Box 312, Madill, Okla. 73446

[21] Appl. No.: 09/168,465

[22] Filed: Oct. 8, 1998

[51] Int. Cl.[7] .................................................. A61B 7/02
[52] U.S. Cl. ........................ 181/131; 181/137; D3/203; 24/3.11; 24/3.6; 224/268; 224/269
[58] Field of Search ................................ 181/131, 137; D3/203; 24/3.6, 3.7, 3.11, 3.12, 3.13; 224/268, 269, 617, 620, 621

[56] References Cited

U.S. PATENT DOCUMENTS

| | | | |
|---|---|---|---|
| D. 344,798 | 3/1994 | Baskin | D24/134 |
| 742,790 | 10/1903 | Jones | 181/131 |
| 1,797,098 | 3/1931 | Minehart | 24/3.6 |
| 1,834,863 | 12/1931 | Palmore | 24/3.6 |
| 2,209,164 | 7/1940 | Kerr | 181/24 |
| 3,772,740 | 11/1973 | Seron | 24/73 R |
| 4,949,432 | 8/1990 | Wisniewski | 24/3 C |
| 5,451,725 | 9/1995 | Goldman | 181/131 |
| 5,539,162 | 7/1996 | Tuttle | 181/131 |
| 5,592,946 | 1/1997 | Eddy | 128/715 |
| 5,692,657 | 12/1997 | Kilo et al. | 224/269 |
| 5,892,233 | 4/1999 | Clement | 250/455.11 |

*Primary Examiner*—Robert E. Nappi
*Assistant Examiner*—Wesley Ashton

[57] ABSTRACT

A stethoscope supporting device is provided including a back plate and front portion for securing a stethoscope to the back plate. Connected to the back plate is a clip for securing the same on an article of clothing.

4 Claims, 3 Drawing Sheets

BELT-MOUNTED STETHOSCOPE SUPPORTING DEVICE

BACKGROUND OF THE INVENTION

1. Field of the Invention

The present invention relates to stethoscope wraps and more particularly pertains to a new belt-mounted stethoscope supporting device for supporting a stethoscope on a belt or piece of clothing of a user to prevent problems associated with carrying the stethoscope about a neck of the user.

2. Description of the Prior Art

The use of stethoscope wraps is known in the prior art. More specifically, stethoscope wraps heretofore devised and utilized are known to consist basically of familiar, expected and obvious structural configurations, notwithstanding the myriad of designs encompassed by the crowded prior art which have been developed for the fulfillment of countless objectives and requirements.

Known prior art stethoscope wraps include U.S. Pat. No. 5,592,946; U.S. Pat. No. 5,451,725; U.S. Pat. No. 5,539,162; U.S. Pat. No. 4,949,432; U.S. Pat. No. Des. 344,798; and U.S. Pat. No. 2,209,164.

In these respects, the belt-mounted stethoscope supporting device according to the present invention substantially departs from the conventional concepts and designs of the prior art, and in so doing provides an apparatus primarily developed for the purpose of supporting a stethoscope on a belt of a user to prevent problems associated with carrying the stethoscope about a neck of the user.

SUMMARY OF THE INVENTION

In view of the foregoing disadvantages inherent in the known types of stethoscope wraps now present in the prior art, the present invention provides a new belt-mounted stethoscope supporting device construction wherein the same can be utilized for supporting a stethoscope on a belt of a user to prevent problems associated with carrying the stethoscope about a neck of the user.

The general purpose of the present invention, which will be described subsequently in greater detail, is to provide a new belt-mounted stethoscope supporting device apparatus and method which has many of the advantages of the stethoscope wraps mentioned heretofore and many novel features that result in a new belt-mounted stethoscope supporting device which is not anticipated, rendered obvious, suggested, or even implied by any of the prior art stethoscope wraps, either alone or in any combination thereof.

To attain this, the present invention generally comprises a planar rectangular back plate with a short top edge, a short bottom edge and a pair of elongated side edges formed therebetween, as shown in FIGS. 1–3. A front portion is also provided having a width and a constant cross-sectional area equal to that of the back plate. Such front portion has a top edge integrally and resiliently coupled to the top edge of the back plate, as best shown in FIGS. 2 & 3. The front portion is defined by a concave upper extent that extends downwardly and outwardly from the back plate to a point level with a midpoint of the back plate. The front portion further has a U-shaped lower extent with a first end coupled to the upper extent. A semi-cylindrical second end of the lower extent is positioned adjacent the back plate at the midpoint thereof. By this structure, the front portion is adapted for releasably receiving the tube of the stethoscope in a coiled orientation. Further included is a clip having a generally planar rectangular configuration with a width equal to that of the back plate and a length approximately ½ that of the back plate. Connected between the clip and the back plate is a coil spring for urging a lower edge of the clip against the back plate. In use, an upper edge of the clip may be biased toward the back plate for urging the lower edge of the clip out of abutment with the back plate.

There has thus been outlined, rather broadly, the more important features of the invention in order that the detailed description thereof that follows may be better understood, and in order that the present contribution to the art may be better appreciated. There are additional features of the invention that will be described hereinafter and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

Further, the purpose of the foregoing abstract is to enable the U.S. Patent and Trademark Office and the public generally, and especially the scientists, engineers and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

It is therefore an object of the present invention to provide a new belt-mounted stethoscope supporting device apparatus and method which has many of the advantages of the stethoscope wraps mentioned heretofore and many novel features that result in a new belt-mounted stethoscope supporting device which is not anticipated, rendered obvious, suggested, or even implied by any of the prior art stethoscope wraps, either alone or in any combination thereof.

It is another object of the present invention to provide a new belt-mounted stethoscope supporting device which may be easily and efficiently manufactured and marketed.

It is a further object of the present invention to provide a new belt-mounted stethoscope supporting device which is of a durable and reliable construction.

An even further object of the present invention is to provide a new belt-mounted stethoscope supporting device which is susceptible of a low cost of manufacture with regard to both materials and labor, and which accordingly is then susceptible of low prices of sale to the consuming public, thereby making such belt-mounted stethoscope supporting device economically available to the buying public.

Still yet another object of the present invention is to provide a new belt-mounted stethoscope supporting device which provides in the apparatuses and methods of the prior art some of the advantages thereof, while simultaneously overcoming some of the disadvantages normally associated therewith.

Still another object of the present invention is to provide a new belt-mounted stethoscope supporting device for supporting a stethoscope on a belt of a user to prevent problems associated with carrying the stethoscope about a neck of the user.

Even still another object of the present invention is to provide a new belt-mounted stethoscope supporting device that includes a back plate and front portion for securing a stethoscope to the back plate. Connected to the back plate is a clip for securing the same on an article of clothing.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be made to the accompanying drawings and descriptive matter in which there are illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein.

DESCRIPTION OF THE PREFERRED EMBODIMENT

Figure 1:
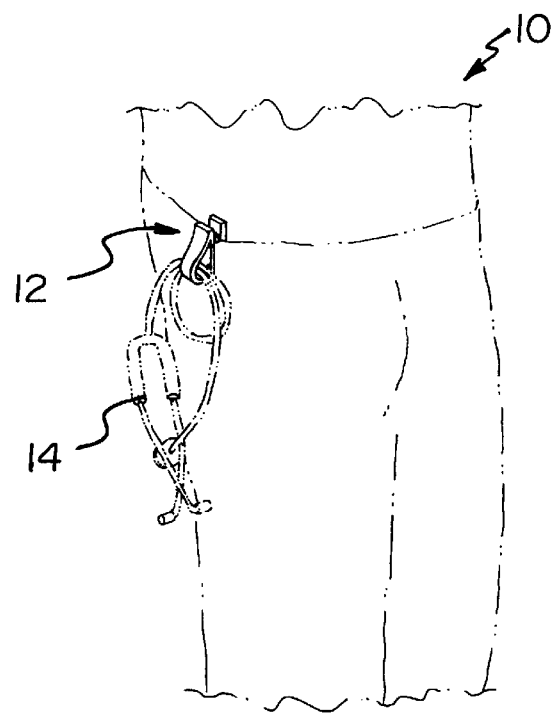
FIG. 1 is a perspective view of a new belt-mounted stethoscope supporting device according to the present invention.

With reference now to the drawings, and in particular to FIGS. 1 through 6 thereof, a new belt-mounted stethoscope supporting device embodying the principles and concepts of the present invention and generally designated by the reference numeral 10 will be described.

The present invention, designated as numeral 10, is a stethoscope supporting device for use with a stethoscope 14 including a pair of ear portions for being releasably received within ears of a user. Such stethoscope further includes a disk-shaped contact portion connected to the ear portions via an elongated tube. In use, the contact portion is adapted for detecting a sound within a patient and transmitting the same to the ear portions.

Figure 2:
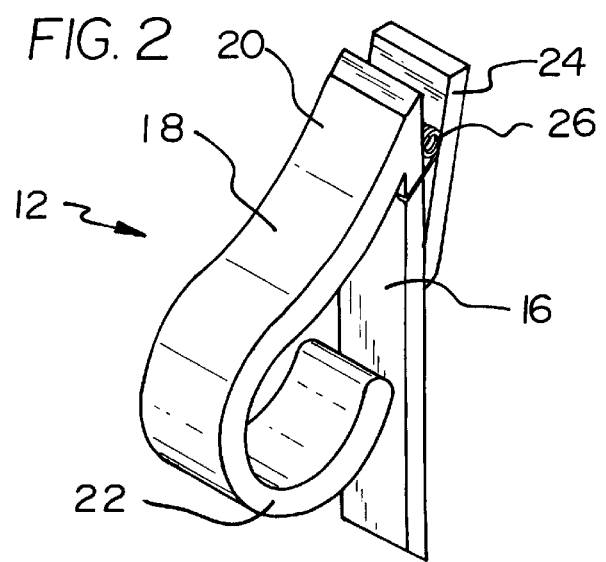
FIG. 2 is a detailed perspective view of the present invention.
Figure 3:
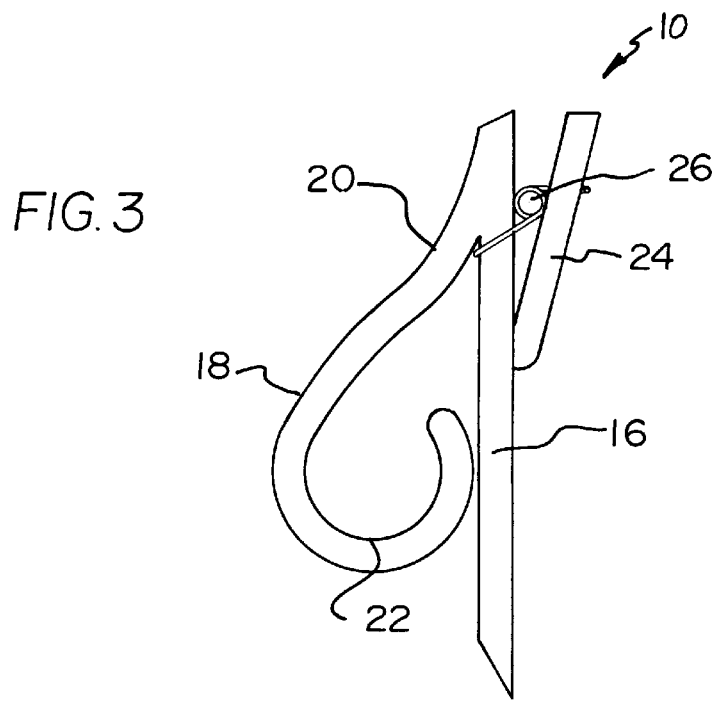
FIG. 3 is a side view of the present invention.

The present invention includes a planar rectangular back plate 16 with a beveled short top edge, a beveled short bottom edge and a pair of elongated side edges formed therebetween, as shown in FIGS. 1–3. Associated therewith is a front portion 18 having a width and a constant cross-sectional area equal to that of the back plate. Such front portion has a top edge integrally and resiliently coupled to the top edge of the back plate, as best shown in FIGS. 2 & 3.

The front portion is defined by a concave upper extent 20 that extends downwardly and outwardly from the back plate to a point level with a midpoint of the back plate. The front portion further has a U-shaped lower extent 22 extending downwardly from the upper extent and inwardly towards the back plate. A semi-cylindrical second end of the lower extent is positioned adjacent the back plate at the midpoint thereof. Ideally, a portion of the lower extent adjacent to the second end abuts the back plate while the second end extends away from the back plate. Note FIG. 3. As such, the back plate lies along a tangent of the lower extent of the front portion.

By this structure, the front portion is adapted for releasably receiving the tube of the stethoscope in a coiled orientation, as shown in FIG. 1. It is important that a cross-sectional diameter of the U-shaped lower extent of the front portion be less than the diameter of the contact portion of the stethoscope in order to prevent the same from inadvertently being removed. Manual removal of the tube may be accomplished by merely biasing the front portion outwardly with respect to the back plate.

Further included is a clip 24 having a generally planar rectangular configuration with a width equal to that of the back plate and a length approximately ½ that of the back plate. Connected between the clip and the back plate is a coil spring 26 for urging a lower edge of the clip against the back plate. In use, an upper edge of the clip may be biased toward the back plate for urging the lower edge of the clip out of abutment with the back plate. As shown in FIG. 3, one end of the coil spring encompasses a central extent of the clip while another end of the coil spring is positioned between the upper extent of the front portion and a top edge of the back plate.

Figure 4:
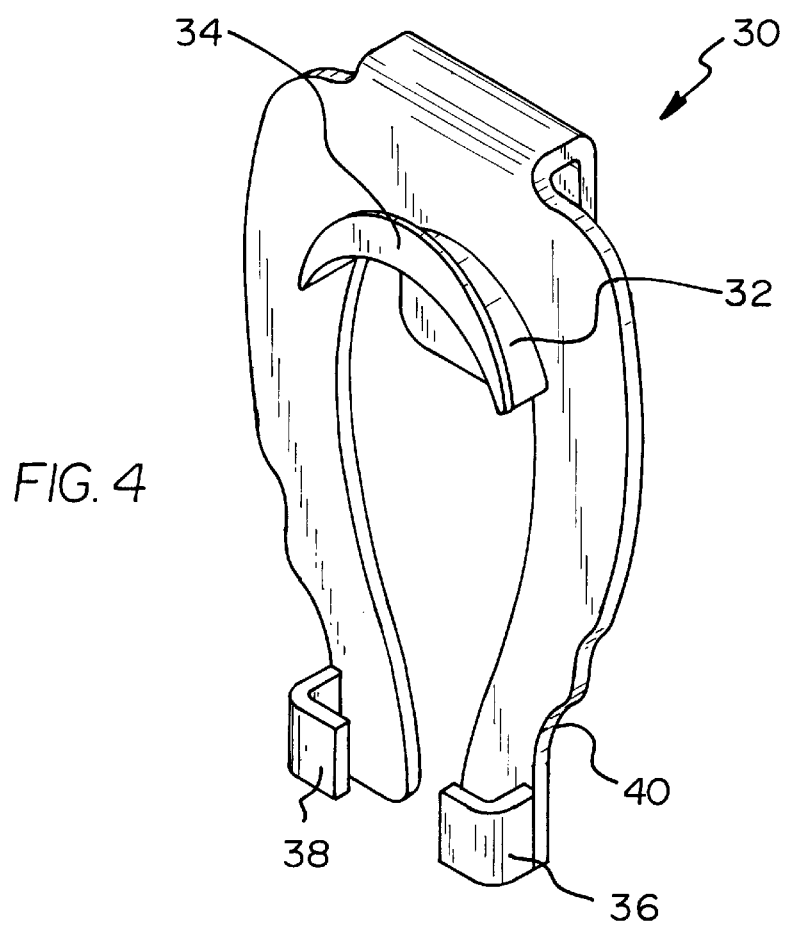
FIG. 4 is a perspective view of an alternate embodiment of the present invention.
Figure 5:
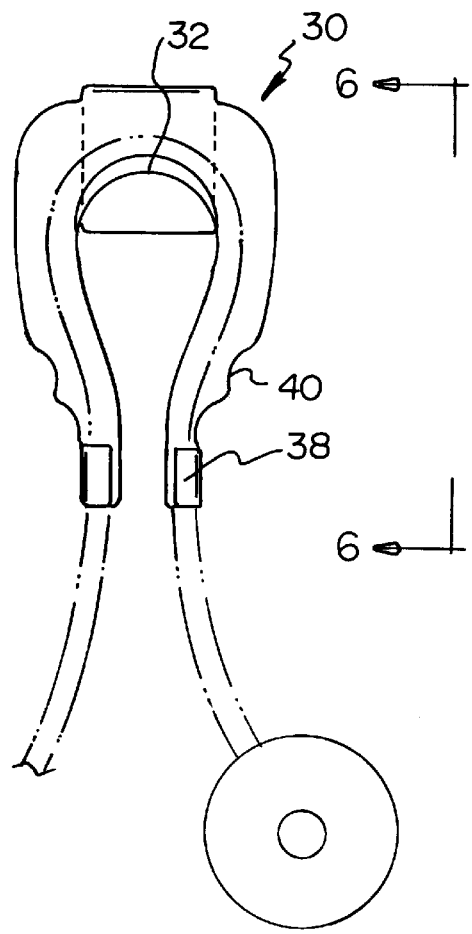
FIG. 5 is a front view of the alternate embodiment of the present invention during use.
Figure 6:
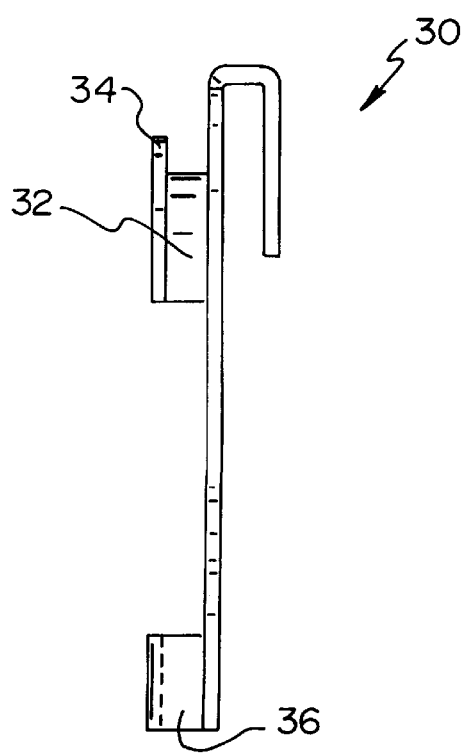
FIG. 6 is a side view of the embodiment of FIGS. 4 & 5.

An alternate embodiment 30 of the present invention is shown in FIGS. 4–6. The planar back plate of such embodiment has a horse-shoe shape. Further, the clip is integrally coupled to the back plate and extends downwardly in parallel relationship therewith. Mounted to a lower edge of an apex of the back plate is an arcuate upper support 32 extending outwardly from the back plate. A peripheral lip 34 is integrally coupled to the support and extends upwardly therefrom for supporting the stethoscope. As shown in FIG. 4, the peripheral lip has tapering sides.

Mounted on outer edges of ends of the back plate is a pair of outwardly extending tabs 36. Such tabs constrain portions of the stethoscope during use, as shown in FIG. 5. Ideally, the tabs each have an inwardly extending flange 38 mounted on an end thereof for better constraining the tube of the stethoscope. The tabs and flanges of the ends of the back plate ideally form inwardly facing parallel grooves. It should be noted that a certain amount of resiliency is exhibited between the ends of the back plate for further constraining the tube of the stethoscope. As shown in FIG. 4, the outer edges of the back plate are preferably tapered and further have a pair of undulations 40 formed therein for allowing a user to better handle the present invention.

In use, the present invention supports a stethoscope on a belt, pocket or any other item of clothing of a user. The present invention works to prevent problems associated with carrying the stethoscope about a neck of the user. Further, by preventing the stethoscope from being exposed to oils commonly found about the neck of the user, the longevity of the stethoscope is improved.

As to a further discussion of the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

I claim:

1. A stethoscope supporting device for supporting a stethoscope from a waist of a user, the supporting device comprising:

a planar rectangular back plate with a short top edge, a short bottom edge and a pair of elongated side edges formed therebetween;

a front portion having a width and a constant cross-sectional area equal to that of the back plate, the front portion having a top edge integrally and resiliently coupled to the top edge of the back plate, a concave upper extent extending downwardly and outwardly from the back plate to a point level with a midpoint of the back plate, a U-shaped lower extent with a first end extending downwardly from the upper extent and inwardly extending towards the back plate, a semi-cylindrical second end of the lower extent being positioned adjacent the back plate at the midpoint thereof for releasably receiving the tube of the stethoscope in a coiled orientation;

a clip having a generally planar rectangular configuration with a width equal to that of the back plate and a length approximately ½ that of the back plate; and a coil spring connected between the clip and the back plate for urging a lower edge of the clip against the back plate, wherein an upper edge of the clip may be biased toward the back plate for urging the lower edge of the clip out of abutment with the back plate.

2. A stethoscope supporting device comprising:

a back plate;

a front portion for securing a stethoscope to the back plate, the front portion being integrally and resiliently mounted to the back plate, the front portion including an upper extent and a lower extent with a U-shaped configuration, wherein a portion of the lower extent abuts the back plate at a midpoint thereof; and a clip connected to the back plate for securing the back-plate to a user.

3. A stethoscope supporting device as set forth in claim 2 wherein the upper extent extends downwardly and outwardly with respect to the back plate.

4. A stethoscope supporting device comprising:

a back plate;

a front portion for securing a stethoscope to the back plate, wherein the front portion includes an arcuate upper support extending outwardly from the back plate with a peripheral lip integrally coupled thereto and extending upwardly therefrom for supporting the stethoscope; and wherein the back plate has a horse-shoe configuration with a pair of ends each having an outwardly extending tab coupled thereto, wherein the tabs are adapted to constrain outward movement by portions of the stethoscope abutting the tabs, the tabs each having an inwardly extending flange mounted on an end thereof for releasably holding portions of the stethoscope against the back plate.

* * * * *